US011908569B2

(12) United States Patent
Himeno

(10) Patent No.: US 11,908,569 B2
(45) Date of Patent: Feb. 20, 2024

(54) ELECTRONIC STICKY NOTE SYSTEM

(71) Applicant: IRYOU JYOUHOU GIJYUTU KENKYUSYO CORPORATION, Fukuoka (JP)

(72) Inventor: Shinkichi Himeno, Fukuoka (JP)

(73) Assignee: IRYOU JYOUHOU GIJYUTU KENKYUSYO CORPORATION, Fukuoka (JP)

(*) Notice: Subject to any disclaimer, the term of this patent is extended or adjusted under 35 U.S.C. 154(b) by 775 days.

(21) Appl. No.: 15/780,972

(22) PCT Filed: Nov. 22, 2016

(86) PCT No.: PCT/JP2016/084526
§ 371 (c)(1),
(2) Date: Jun. 1, 2018

(87) PCT Pub. No.: WO2017/094554
PCT Pub. Date: Jun. 8, 2017

(65) Prior Publication Data
US 2018/0268932 A1 Sep. 20, 2018

(30) Foreign Application Priority Data

Dec. 2, 2015 (JP) .................................. 2015-235537
Sep. 6, 2016 (JP) .................................. 2016-173309

(51) Int. Cl.
*G16H 40/20* (2018.01)
*G06F 3/0481* (2022.01)
(Continued)

(52) U.S. Cl.
CPC .......... *G16H 40/20* (2018.01); *G06F 3/0481* (2013.01); *G06F 40/169* (2020.01);
(Continued)

(58) Field of Classification Search
CPC .................... G06Q 50/24; G16H 10/00–80/00
(Continued)

(56) References Cited

U.S. PATENT DOCUMENTS 9,245,251 B2\* 1/2016 Lyle ........................ G06Q 10/10
10,297,343 B1\* 5/2019 Wartenfeld ............ G16H 70/00
(Continued)

FOREIGN PATENT DOCUMENTS

JP   H04-310176    11/1992
JP   2001-22749    1/2001
(Continued)

OTHER PUBLICATIONS

P. Pirarthani and S. Murugan, "Synchronization of sticky notes using cloud," 2015 International Conference on Communications and Signal Processing (ICCSP), Melmaruvathur, 2015, pp. 1497-1500, doi: 10.1109/ICCSP.2015.7322764. (Year: 2015).\*
(Continued)

*Primary Examiner* — Christopher L Gilligan
*Assistant Examiner* — Bennett Stephen Erickson
(74) *Attorney, Agent, or Firm* — Hamre, Schumann, Mueller & Larson, P.C.

(57) ABSTRACT

An electronic record management system includes a server and a plurality of electronic record display terminals in electronic communication with the server. Each electronic record display terminal includes a monitor screen. The server stores a list of cases each with an associated case identifier, stores a list of staff members each with an associated staff identifier, and stores documents associated with each case. The server creates an electronic sticky note and a display format of the electronic sticky note. The server electronically communicates with at least one of the electronic record display terminals to cause the monitor screen of the at least one electronic record display terminal to
(Continued)

display an electronic record of one of the cases along with the electronic sticky note overlaid over a portion of the electronic record.

14 Claims, 5 Drawing Sheets

(51) Int. Cl.
*G06Q 10/10* (2023.01)
*G06Q 10/109* (2023.01)
*G06F 40/169* (2020.01)
*G06F 40/194* (2020.01)
*G06F 40/197* (2020.01)
*G16H 10/60* (2018.01)

(52) U.S. Cl.
CPC .......... *G06F 40/194* (2020.01); *G06F 40/197* (2020.01); *G06Q 10/10* (2013.01); *G06Q 10/109* (2013.01); *G16H 10/60* (2018.01)

(58) Field of Classification Search
USPC .......................................................... 705/2–3

See application file for complete search history.

(56) References Cited

U.S. PATENT DOCUMENTS

| | | | |
|---|---|---|---|
| 2002/0138582 A1* | 9/2002 | Chandra | G06Q 10/107 |
| | | | 709/206 |
| 2008/0300922 A1* | 12/2008 | Forgue | G16H 10/60 |
| | | | 705/3 |
| 2011/0115825 A1* | 5/2011 | Tetsuhashi | G06F 40/169 |
| | | | 345/672 |
| 2020/0294640 A1* | 9/2020 | Ginsburg | G16H 40/20 |

FOREIGN PATENT DOCUMENTS

| | | |
|---|---|---|
| JP | 2001-142997 | 5/2001 |
| JP | 2005-251082 | 9/2005 |
| JP | 2011-076451 | 4/2011 |
| JP | 5233524 | 7/2013 |

OTHER PUBLICATIONS

International Search Report and Written Opinion, International Patent Application No. PCT/JP2016/084526, dated Jan. 10, 2017, with English translation of Search Report (7 pages).

Shinkichi Himeno, U.S. Appl. No. 15/574,694, filed Nov. 16, 2017 (38 pages).

Shinkichi Himeno, U.S. Appl. No. 15/747,384, filed Jan. 24, 2018 (37 pages).

* cited by examiner

EXAMPLE OF CASE ID MANAGING UNIT

|   | CASE NUMBER | ADMINISTRATOR ID | NAME | AGE | SEX | · · · · · |
|---|---|---|---|---|---|---|
| ✓ | 201 | 1536 | KAZUO YAMADA | 65 | MALE | · · · · · |
| ✓ | 202 | 2963 | TARO KAWAGUCHI | 82 | MALE | · · · · · |
| ✓ | 203 | 1764 | YUZO TANAKA | 43 | MALE | · · · · · |
| ✓ | · | · | · | · | · | · · · · · |
| ✓ | · | · | · | · | · | · · · · · |
| ✓ | · | · | · | · | · | · · · · · |
| ✓ | · | · | · | · | · | · · · · · |
|   | 301 | 2018 | JUNKO YAMANAKA | 25 | FEMALE | · · · · · |
|   | 302 | 1829 | SOKO HANADA | 68 | FEMALE | · · · · · |
|   | · | · | · | · | · | |

Fig. 2

STAFF ID MANAGING UNIT

| | STAFF ID | NAME | TYPE OF JOB | WORK PLACE | ... |
|---|---|---|---|---|---|
| ✓ | 1865 | TARO YAMADA | DOCTOR | MEDICAL OFFICE | ... |
| ✓ | 2493 | HANAKO YAMAMOTO | NURSE | T 2 | ... |
| ✓ | 3765 | REIKO TAJIMA | NURSE | T 2 | ... |
| ✓ | 0824 | KAZUE TSUJIMOTO | CAREGIVER | T 2 | ... |
| ✓ | 8943 | AIKO HARIMOTO | MEDICAL ADMINISTRATIVE SECTION | RECEPTION | ... |
| | 2111 | YUMI YAMASHITA | CAREGIVER | T 3 | ... |
| | 2356 | YUMI TANAKA | NURSE | T 3 | ... |
| ✓ | 3164 | HANAKO YOSHIOKA | REHABILITATION SECTION | CARE ROOM | ... |
| | 2910 | ICHIRO TOYAMA | NURSE | T 4 | ... |
| | ⋮ | ⋮ | ⋮ | ⋮ | ⋮ |

ELECTRONIC STICKY NOTE SYSTEM

TECHNICAL FIELD

The present invention relates to an electronic sticky note system that prevents omission of works and mistakes by giving reminders to every staff member while efficiently making records and work instructions using a computer network and, in particular, an electronic sticky note system for an electronic medical record of a patient, a resident, or the like created in medical agencies, care agencies, and welfare agencies.

BACKGROUND ART

In the field of medical care and nursing care, members of many types of jobs, such as medical doctors, nurses, and caregivers are involved with respect to a single patient/user and the observation records, instructions associated with works, work reports, and the like are created as medical records. Works as a team with multiple types of jobs advance by filling in and referring to such medical records. In recent years, electronic medical records have become widespread, making it possible to efficiently create records and work instruction documents using a computer network.

As the electronic medical records are used at a higher level, the type and quantity of documents to be created continues to increase and it becomes realistically difficult to read through all the documents even for the staff members involved with a specific patient/user. Especially in cooperative operations involving a plurality of types of jobs with time lags, errors such as omission of works are easy to occur due to mismatch of communication. For example, in a case where a promise is made, when an outpatient consultation is finished, to draw blood immediately after the reception at the next time such that an inspection result is prepared before the examination, a nurse in the examination room and an administrative staff member at the reception have different types of jobs and additionally, specific working staff members are different at the next visit in many cases. For this reason, there have been frequent occurrences in which, for example, when a patient visits the next time, a receptionist did not know that blood drawing should be done before the examination and unnecessarily kept the patient waiting without doing anything until the examination, such that a blood drawing was quickly arranged thereafter. Such a case not only earns the distrust of patients but also easily results even in a medical accident in some cases.

In order to prevent a work error as in the previous section, in the case of a paper medical record, a paper sticky note such as "blood drawing before examination at next visit" has been stuck on the front cover of the medical record and has been peeled off after the work is completed. In the case of the electronic medical record, since a paper medical record cannot be used, a sticky note is electronically created such that the contents of the sticky note are displayed on a monitor screen when a relevant medical record is called.

There is a similar necessity also in non-medical companies and the electronic sticky note for preventing mismatch of communication is useful when a large number of staff members are involved in a case. In this case, a case ID such as a document reception number is used instead of a patient ID of the electronic medical record.

As the prior art literatures related to the present application of the electronic sticky note, the techniques of Patent Literatures 1 to 3 are known.

CITATION LIST

Patent Literature

Patent Literature 1: JP 2001-142997 A
Patent Literature 2: JP 2005-251082 A
Patent Literature 3: JP 5233524 B2

SUMMARY OF INVENTION

Technical Problem

In Patent Literature 1, a creator and creation date and time of a created electronic sticky note are automatically recorded on the electronic sticky note, whereby efforts of manual creation of such records are saved.

In Patent Literature 2, electronic sticky note data is created separately from an electronic medical record and medical expense claim software (receipt computer) and, when data of a relevant patient is displayed on the electronic medical record or the receipt computer, the contents of the electronic sticky note are also displayed.

In Patent Literature 3, in a case where an important addition or change requiring an attention of a medical doctor in charge is made to the contents of an electronic medical record of a certain patient, in order that the medical doctor does not inadvertently omit recognition, the contents of the electronic sticky note are also displayed when this medical doctor opens the electronic medical record of this patient to prompt the medical doctor to give the attention.

Regardless of any of the electronic sticky notes mentioned above, when actually put in operation, many sticky notes are created by each type of job and it is even enough to cover the entire screen when the electronic medical record is opened. In addition to becoming obstacles to referring to electronic medical record, there has been a difficulty in that oversight of electronic sticky notes is even likely to occur because there are too many electronic sticky notes. This is because even electronic sticky notes that are important for a certain type of job but irrelevant to other types of jobs are displayed uniformly to all the users of the electronic medical record.

On the contrary, if it is attempted to display an electronic sticky note concerning the same caution on medical records of all hospitalized patients, it has been necessary to open every applicable electronic medical record one by one and take time to create electronic sticky notes of the same contents.

Furthermore, when a certain staff member changes or deletes an electronic sticky note that is shared by a plurality of staff members, the contents of this electronic sticky note are suddenly changed or disappear to other staff members, such that there has been a difficulty in that confusion is brought about as a consequence.

The present invention has been made to solve such conventional disadvantages and it is an object thereof to provide an electronic sticky note system that is convenient and prevents an oversight from occurring by limiting a user to whom an electronic sticky note is displayed to share information and displaying only a minimum number of electronic sticky notes, in addition, by enabling collective display setting at once for a plurality of cases requiring display of an electronic sticky note, and furthermore, by preventing confusion even when the content of an electronic sticky note is changed or deleted, by notifying also other staff members who share the electronic sticky note of the fact of the change or deletion.

Solution to Problem

As a means for achieving the above object, in record management for a plurality of cases involving a plurality of staff members, an electronic sticky note system according to claim 1 includes: a case ID managing unit that manages IDs of the plurality of cases; a document type managing unit that manages a plurality of document types constituting a case record; a case-specific document-type-specific recording unit that manages a record of each case for each document type; a staff ID managing unit that manages IDs of the plurality of staff members; an electronic sticky note creating unit that creates and records contents of an electronic sticky note together with a display format; an electronic sticky note display condition setting unit that sets and records a condition for displaying the electronic sticky note; an electronic sticky note display permission determining unit that determines whether the electronic sticky note matches the "condition for displaying" at the time of displaying the case record; and an electronic sticky note display unit that displays the electronic sticky note on a monitor screen together with the case record in a case where display of the electronic sticky note is permitted.

In an electronic sticky note system according to claim 2, the electronic sticky note display condition setting unit according to the electronic sticky note system according to claim 1 is capable of setting, as a condition for displaying for a certain staff member when referring to a certain case record, either an attribute of the case, an attribute of the staff member, a type of a document to be referred to, or a date of reference, or a combination of the conditions.

In an electronic sticky note system according to claim 3, the electronic sticky note system according to claim 1 or 2 further includes an electronic sticky note change/deletion notifying unit that, when a certain staff member changes or deletes an already created electronic sticky note, notifies a staff member other than the staff member, to whom the electronic sticky note is to be displayed, that the electronic sticky note has been changed or deleted.

Advantageous Effects of Invention

Since the electronic sticky note system according to claim 1 includes the case ID managing unit that manages IDs of the plurality of cases, the document type managing unit that manages a plurality of document types constituting a case record, the case-specific document-type-specific recording unit that manages a record of each case for each document type, and the staff ID managing unit that manages IDs of the plurality of staff members, a range for displaying the electronic sticky note can be set in accordance with an attribute of a case, a type of a document to be created, and a staff member involved with a patient/user.

Since the electronic sticky note creating unit that creates and records contents of an electronic sticky note together with a display format and the electronic sticky note display condition setting unit that sets and records a condition for displaying the electronic sticky note are included, a display format and a display condition of the electronic sticky note can be arbitrarily set.

Since the electronic sticky note display permission determining unit that determines whether the electronic sticky note matches the "condition for displaying" at the time of displaying the case record is included, the electronic sticky note is displayed on a monitor screen together with the case record in regard to a case and a staff member matching the "condition for displaying".

Since the electronic sticky note system according to claim 2 is capable of setting, as a condition for displaying for a certain staff member when referring to a certain case record, either an attribute of the case, an attribute of the staff member, a type of a document to be referred to, or a date of reference, or a combination of the conditions, the electronic sticky note can be displayed to a limited staff member who needs to share information with the electronic sticky note.

Since the electronic sticky note system according to claim 3 further includes an electronic sticky note change/deletion notifying unit that, when a certain staff member changes or deletes an already created electronic sticky note, notifies a staff member other than the staff member, to whom the electronic sticky note is to be displayed, that the electronic sticky note has been changed or deleted, the fact of the change or deletion is notified also to other staff member who shares the electronic sticky note even if the contents of the electronic sticky note are changed or deleted.

BRIEF DESCRIPTION OF DRAWINGS

FIG. 2 is an explanatory diagram of an example of a case ID managing unit.

FIG. 3 is an explanatory diagram of an example of a staff ID managing unit.

DESCRIPTION OF EMBODIMENTS

Figure 1:
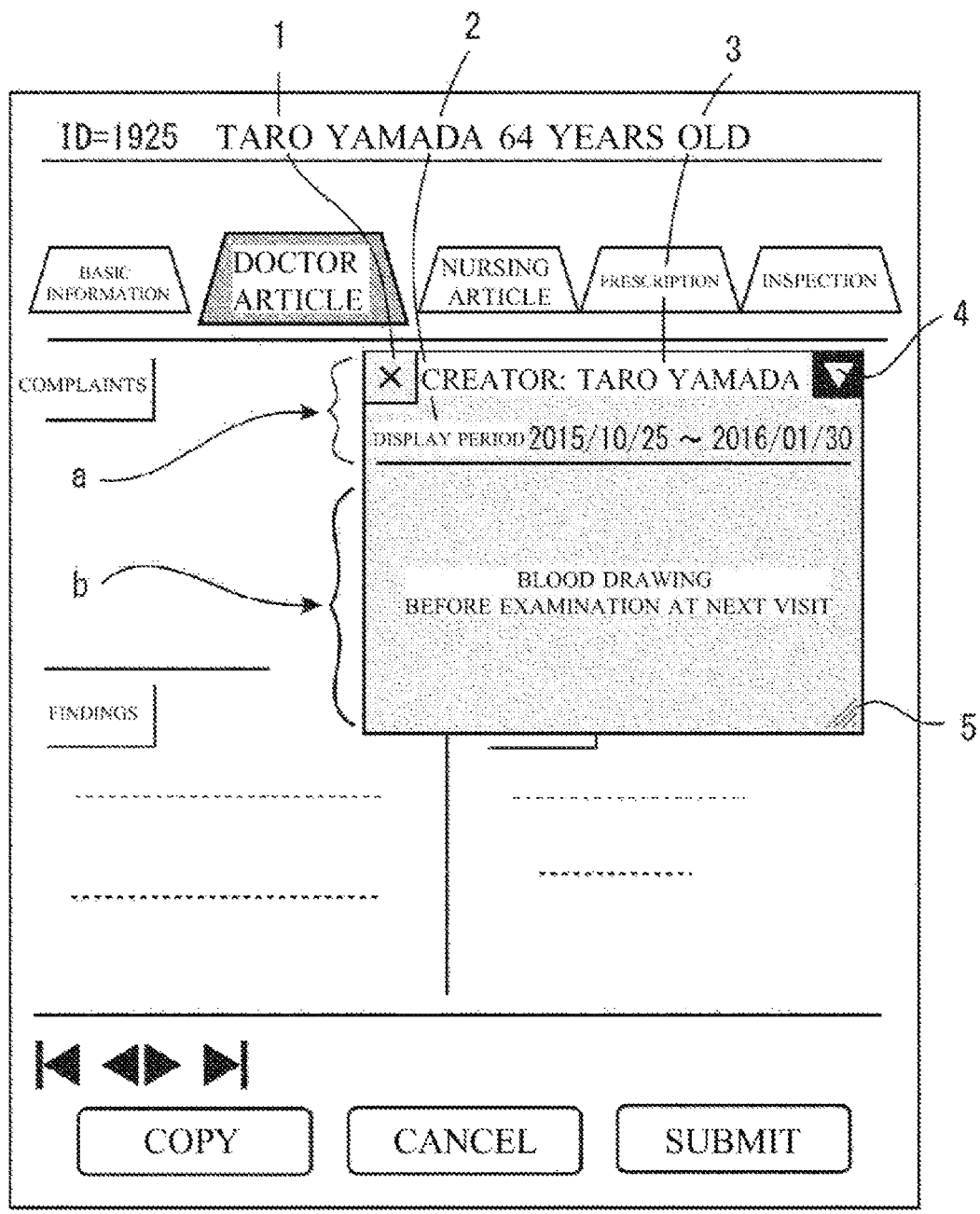
FIG. 1 is an explanatory diagram of an example of an electronic sticky note.

FIG. 1 is an example in which an electronic sticky note is also displayed on a screen of an electronic medical record. A creator name, a display period, and the like are presented in an upper part of the electronic sticky note and a ∇ icon on the upper right is an icon for opening a screen of an electronic sticky note display condition setting unit. A display size change icon for changing the display size is on the lower right and an electronic sticky note hide icon for hiding the electronic sticky note is on the upper left.

Contents such as "blood drawing before examination at next visit" are displayed in a lower part of the electronic sticky note such that a staff member of a medical administrative section or a nurse at an outpatient reception desk who saw this electronic sticky note can guide the patient to a blood drawing room immediately and ensure that the result is ready before being called into an examination room.

In this manner, by utilizing the electronic sticky note, a plurality of types of jobs can share information to implement smooth work.

FIG. 2 is an explanatory diagram of a case ID managing unit.

Here, an inpatient list is used as the case ID managing unit. Check boxes as to whether to display the electronic sticky notes are on the far left and a room number, a patient ID, a patient name, and the like are listed for each patient. In a case where the same electronic sticky note needs to be attached for all patients, simply, all patients are checked and, in a case where only a particular patient is concerned, only that patient is checked.

In a case where a patient who is hospitalized in a certain ward (T2 in the example) is concerned, it is only necessary to check a patient with a room number belonging to the T2 ward. In this manner, with the case ID managing unit, it is possible to set whether to permit the display of the electronic sticky note not only for just a case for which the electronic sticky note has been created but also for a case other than this case in accordance with attributes such as the room number and the name.

In addition, case attributes such as sex and age may be used. As alternatives, another information source may be referred to in addition to the attributes registered in the case ID managing unit.

In this example, the inpatient list is used as the case ID managing unit, but a list of outpatients on a certain day, a list of patients by disease, and the like may be selected as necessary.

FIG. 3 is an explanatory diagram of a staff ID managing unit.

Check boxes as to whether to display the electronic sticky notes are on the far left and a staff ID, a name, a type of job, a work place, and the like are listed for each staff member.

In a case where the electronic sticky note needs to be displayed for all staff members, simply, all staff members are checked and, in a case where only a particular staff member (for example, exclusively a user him/herself) is concerned, only that staff member is checked.

If only a staff member who works at a certain ward (T2 in the example) is concerned, it is only necessary to check a staff member relevant to the T2 ward. In this manner, with the staff ID managing unit, it is possible to set whether to permit the display of the electronic sticky note in accordance with attributes such as a type of job and a work place of staff.

By combining FIGS. 2 and 3, a range for displaying a certain electronic sticky note can be set to any patient group or staff group.

Figure 4:
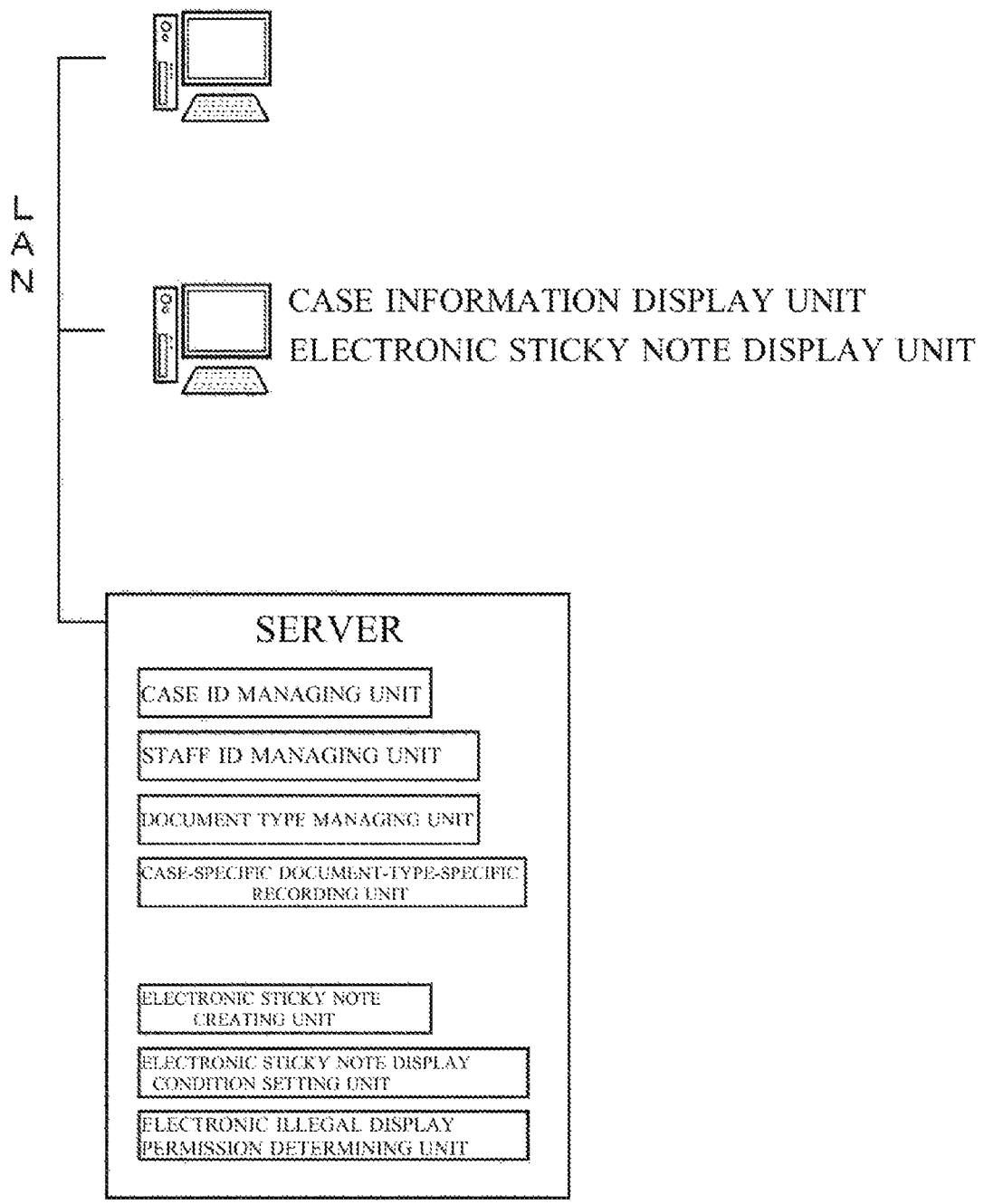
FIG. 4 is an explanatory diagram of a configuration of an electronic sticky note system.

FIG. 4 illustrates a network configuration of electronic medical record display terminals via a server and a local area network (LAN).

The server contains the case ID managing unit such as a patient ID master or an inpatient ID master as illustrated in FIG. 2.

Each case is a collection of a plurality of types of documents such as doctor articles and nursing articles. A document type managing unit manages a list of these document types and lists, attributes, and formats of entries constituting each document type.

A case-specific document-type-specific recording unit records a created document for each case and each document type.

The staff ID managing unit manages a list of staff as illustrated in FIG. 3 and attributes of each staff member.

The staff member is authenticated by inputting the staff ID and password during login operation to a case management system.

The terminal connected via the LAN includes a case information display unit that displays information on a case and an electronic sticky note display unit to display information on a case and an electronic sticky note concerning this case. In FIG. 4, only elements necessary for the explanation of the present invention are extracted and illustrated.

Editing means, transmission/reception means, and the like for case information normally included in the server and terminals are not illustrated. The server is not limited to being installed in the LAN, but a cloud environment such as another facility or a data center may be used. The LAN can be wired or wireless.

An electronic sticky note creating unit creates and records the contents of the electronic sticky note together with the display format.

The electronic sticky note display condition setting unit sets and records a condition for displaying a specific electronic sticky note.

An electronic sticky note display permission determining unit determines whether an electronic sticky note matches a "condition for displaying" and, in a case where the display of the electronic sticky note is permitted, uses the electronic sticky note display unit to display this electronic sticky note on a monitor screen.

The "condition for displaying" mentioned above includes, in addition to the attribute of a relevant case as illustrated in FIG. 2 and the attribute of a relevant staff member as illustrated in FIG. 3, a condition for displaying an electronic sticky note when a particular document type among the document types constituting a relevant case is referred to, a condition for displaying an electronic sticky note in a case where the date of execution of the reference falls within a particular date range, and an arbitrary combination of these conditions. Furthermore, the present invention is not limited thereto and an electronic sticky note display condition other than the above may be separately set.

In FIG. 4, electronic sticky note data created by the electronic sticky note creating unit and the electronic sticky note display condition setting unit is recorded separately from document data recorded by the case-specific document-type-specific recording unit. However, if the attribute of a relevant case as illustrated in FIG. 2 is not used as the electronic sticky note display condition, the display of the electronic sticky note is limited to when this case is referred to and therefore the electronic sticky note data may be recorded in the document data of this case.

The illustration in FIG. 4 is based on the image of a conventional server client system in which processing software is also installed in the terminal. However, an approach that does not install the processing software in the terminal using the currently widespread mechanism such as software as a service (SaaS) or virtual terminal can be said to be more preferable because maintenance costs can be reduced.

Although the electronic sticky note creating unit is normally started up after a certain case record is opened, the electronic sticky note creating unit may be independently started up without opening a case information record such that an electronic sticky note is created and thereafter the electronic sticky note display condition is set.

If a certain staff member modifies or deletes an already created electronic sticky note and thus the contents of the electronic sticky note is suddenly altered or no longer displayed, the other staff member progresses the work with the previous contents of the electronic sticky note or is confused by the fact that the electronic sticky note has unexpectedly disappeared. In order to prevent this difficulty, an electronic sticky note change/deletion notifying unit that notifies a staff member to whom the electronic sticky note is to be displayed, other than the staff member who has changed or deleted the electronic sticky note, that this electronic sticky note has been changed or deleted is necessary.

Figure 5:
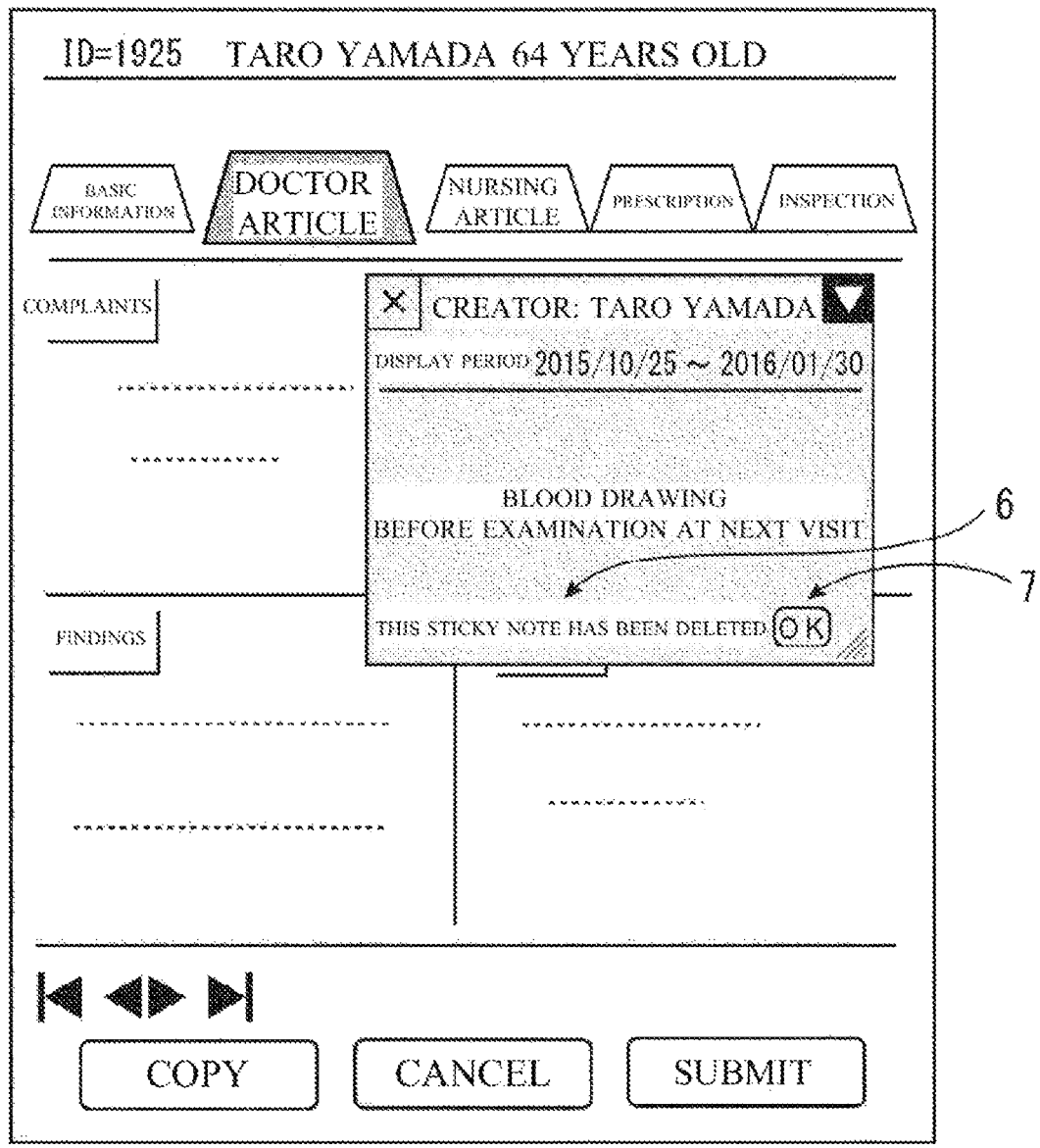
FIG. 5 is an explanatory diagram of an electronic sticky note change/deletion notifying unit.

In the example illustrated in FIG. 5, a message such as "this sticky note has been deleted" or "contents of this sticky note has been changed" is displayed in the electronic sticky note and, when an "OK" button is clicked, the display of this electronic sticky note disappears in the case of deletion, or alternatively, this electronic sticky note is redisplayed with the changed new contents in the case of modification. In this case, it is necessary to hold the contents of the electronic sticky note before the deletion or modification and, at the same time, to manage the state of "clicked"/"not yet clicked" on the "OK" button in the list of staff members to whom this electronic sticky note is to be displayed in FIG. 3. The latest state of this electronic sticky note is displayed to a staff member who has already clicked on the "OK" button and the contents of the electronic sticky note before the deletion or modification are displayed to a staff member who has not clicked yet, together with the above message regarding the deletion or change.

In some cases, a staff member to whom this electronic sticky note is to be displayed may be notified of the fact of the change or deletion by any means such as an e-mail or a short message. In this case, the electronic sticky note is always displayed in the latest state only.

Although an embodiment has been described so far using the electronic medical record used in medical and nursing care as an example, specific structures of the present invention are not limited to the above embodiment, and design changes and the like within the scope of the invention are included in the present invention.

For example, for a case record of a case managed by some ID, such as a service record of a hotel or a service industry managed by a customer ID, an assessment record of an application case managed by a reception number ID, and a progress record for construction, development, or the like managed by a project ID, it is possible to use the electronic sticky note similarly to the electronic sticky note for the electronic medical record.

REFERENCE SIGNS LIST a Attribute area
b Content display area
1 Electronic sticky note hide icon
2 Display period
3 Creator display
4 Condition setting icon
5 Display size change icon
6 Delete/change message
7 Delete/change message confirmation button

The invention claimed is:

1. An electronic record management system, comprising:
a server;
a plurality of electronic record display terminals in electronic communication with the server, each electronic record display terminal including a monitor screen that can display a graphical user interface;
the server stores a list of a plurality of cases each with an associated case identifier, stores a list of a plurality of staff members each with an associated staff identifier, and stores a plurality of documents associated with each case;
the server is configured to create an electronic sticky note and a display format of the electronic sticky note;
the server stores at least one condition for displaying the electronic sticky note; and
the server electronically communicates with at least one of the electronic record display terminals to cause the monitor screen of the at least one electronic record display terminal to display an electronic record of one of the cases along with the electronic sticky note overlaid over a portion of the electronic record, the displayed electronic sticky note including an original message, and the displayed electronic sticky note displays a change message along with the original message, the change message indicating that the original message has been changed or that the electronic sticky note has been deleted.

2. The electronic record management system of claim 1, wherein the server and the plurality of electronic record display terminals are in electronic communication via a local area network.

3. The electronic record management system of claim 2, wherein the local area network is wired or wireless.

4. The electronic record management system of claim 1, wherein the server is a cloud server.

5. The electronic record management system of claim 1, wherein the electronic sticky note also displays a confirmation button associated with and adjacent to the change message that must be selected before the original message is changed or before the electronic sticky note is deleted.

6. The electronic record management system of claim 1, wherein the electronic sticky note displayed on the monitor screen further includes a display period.

7. The electronic record management system of claim 6, wherein the electronic sticky note displayed on the monitor screen further includes a name of the creator of the electronic sticky note.

8. An electronic record management method, comprising:
at a server, creating an electronic sticky note and a display format of the electronic sticky note;
transmitting an electronic record and the electronic sticky note and the display format to at least one electronic record display terminal to cause a monitor screen of the at least one electronic record display terminal to display the electronic record of a case along with the electronic sticky note overlaid over a portion of the electronic record, wherein the displayed electronic sticky note includes an original message;
receiving at the server a change to the original message or deletion of the electronic sticky note;
the server generating a change message and sending the change message to the at least one electronic record display terminal, the change message being displayed on the electronic sticky note along with the original message, the change message indicating that the original message has been changed or that the electronic sticky note has been deleted.

9. The electronic record management method of claim 8, wherein the server and the at least one electronic record display terminal is in electronic communication via a local area network.

10. The electronic record management method of claim 9, wherein the local area network is wired or wireless.

11. The electronic record management method of claim 8, wherein the server is a cloud server.

12. The electronic record management method of claim 8, wherein the electronic sticky note also displays a confirmation button associated with and adjacent to the change message; and upon selection of the confirmation button, changing the original message that is displayed on the monitor screen or deleting the electronic sticky note so that the electronic sticky note is no longer displayed on the monitor screen.

13. The electronic record management method of claim 8, further comprising including a display period on the electronic sticky note that is displayed on the monitor screen.

14. The electronic record management method of claim 8, further comprising including a name of the creator of the electronic sticky note on the electronic sticky note that is displayed on the monitor screen.

\* \* \* \* \*